United States Patent
Barman

(10) Patent No.: US 8,601,628 B2
(45) Date of Patent: Dec. 10, 2013

(54) ELECTRIC TOOTHBRUSH

(75) Inventor: Ole Barman, Bergen (NO)

(73) Assignee: Petosan AS, Haukeland (NO)

( * ) Notice: Subject to any disclaimer, the term of this patent is extended or adjusted under 35 U.S.C. 154(b) by 820 days.

(21) Appl. No.: 12/451,103

(22) PCT Filed: Apr. 21, 2008

(86) PCT No.: PCT/NO2008/000144
§ 371 (c)(1),
(2), (4) Date: Apr. 14, 2010

(87) PCT Pub. No.: WO2008/130246
PCT Pub. Date: Oct. 30, 2008

(65) Prior Publication Data
US 2010/0199445 A1    Aug. 12, 2010

(30) Foreign Application Priority Data

Apr. 23, 2007 (NO) .................................. 20072079

(51) Int. Cl.
*A61C 17/22* (2006.01)
*A46B 13/02* (2006.01)

(52) U.S. Cl.
USPC ......................................................... 15/22.1

(58) Field of Classification Search
USPC ......................................................... 15/22.1
See application file for complete search history.

(56) References Cited

U.S. PATENT DOCUMENTS

| | | | |
|---|---|---|---|
| 5,253,382 A * | 10/1993 | Beny | 15/22.1 |
| 5,987,681 A * | 11/1999 | Hahn et al. | 15/22.1 |
| 6,920,659 B2 * | 7/2005 | Cacka et al. | 15/22.1 |
| 7,240,390 B2 * | 7/2007 | Pfenniger et al. | 15/22.1 |
| 7,886,393 B2 * | 2/2011 | Sorrentino | 15/22.1 |
| 2006/0101598 A1 * | 5/2006 | Fujimoto et al. | 15/22.2 |

FOREIGN PATENT DOCUMENTS

| | | | |
|---|---|---|---|
| JP | 3-261407 | * | 11/1991 |
| JP | 7-299416 | * | 11/1995 |
| JP | 2003-93415 | * | 4/2003 |
| JP | 2003-245288 | * | 9/2003 |
| JP | 2003-339744 | * | 12/2003 |
| JP | 2005-296515 | * | 10/2005 |
| JP | 2006-141513 | * | 6/2006 |

* cited by examiner

*Primary Examiner* — Mark Spisich
(74) *Attorney, Agent, or Firm* — Abelman, Frayne & Schwab

(57) ABSTRACT

An electric toothbrush is described, comprising a vibrating brush head (20) and a main unit (6) with a vibrator motor (2) for transfer of vibrating power to the brush head (20), and also a battery (9) connected to an on/off switch (7) for operation of the vibrator motor (2). The vibrator motor (2) is not rigidly secured to the main unit (6) with help of a quick coupling (Ia), and that the vibrator motor (2) is at least partially contained in a rubber covering (5) that surrounds the main unit (6).

6 Claims, 3 Drawing Sheets

ELECTRIC TOOTHBRUSH

CROSS REFERENCE TO RELATED APPLICATION

This application claims benefit under 35. U.S.C. §371 to international application No. PCT/NO2008/000144, filed on Apr. 21, 2008.

The present invention relates to an electric toothbrush, comprising a vibrating brush head and a main unit with a vibrator motor for transfer of vibrating power to the brush head, and also a battery connected to an on/off switch for operation of the vibrator motor, in that the vibrator motor is not secured rigidly to the main unit with the help of a quick coupling.

From prior art, US 2003/0031979 A1, EP 460610 A1 and U.S. Pat. No. 2,278,365 can be brought forward, among others. All these publications relate to electric toothbrushes with a motor for transfer of vibrations.

It is an object of the present invention to provide an electric toothbrush which is moisture-proof and which provides improved vibrating power to the brush head of the toothbrush and reduced vibration to the toothbrush handle.

Said objects are achieved with an electric toothbrush as described below, in that the vibrator motor is at least partially housed within a rubber covering that surrounds the main unit.

Alternative preferred embodiments are also described below and set forth in the claims.

The rubber covering can be arranged to reduce the vibration that is transferred to the main unit from the vibrator motor. The rubber covering preferably covers most of the main unit and at least part of the vibrator motor so that a seal against moisture is provided.

The vibrator motor is preferably fitted in a motor frame which is secured to the main unit with the help of one or more quick locks that are forced into grooves or openings in a forward part of the main unit. The motor frame can comprise an internal spacer which is arranged to press against said quick lock(s) for locking of the motor frame. Furthermore, a pin can be arranged in the motor frame.

The invention shall now be described in more detail with reference to the enclosed drawings, in which FIG. 1 shows a section of a main unit of an electric toothbrush according to the invention.

Figure 1:
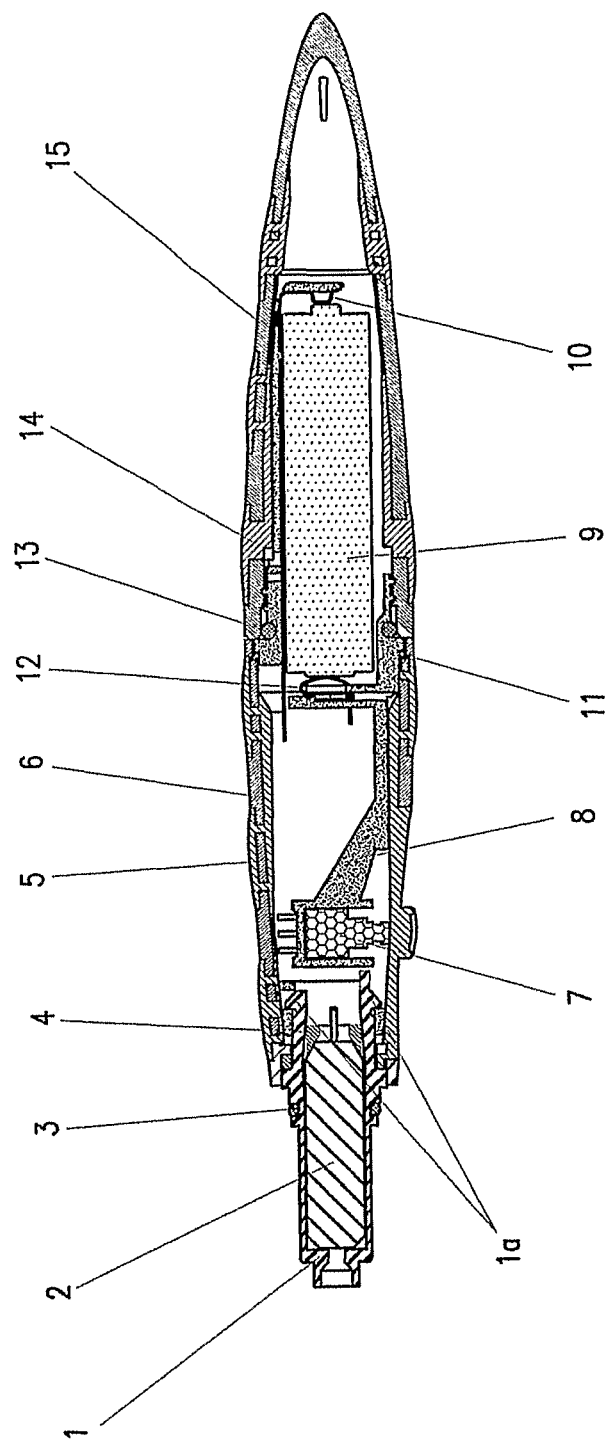
Figure 2:
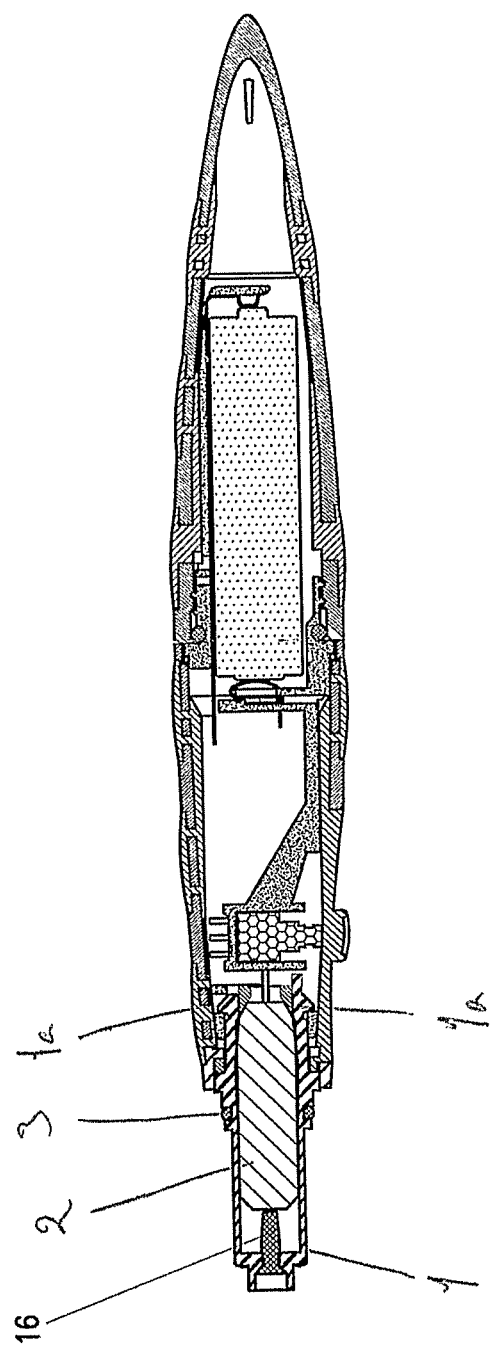
FIG. 2 shows a corresponding section of the main unit.
Figure 3:
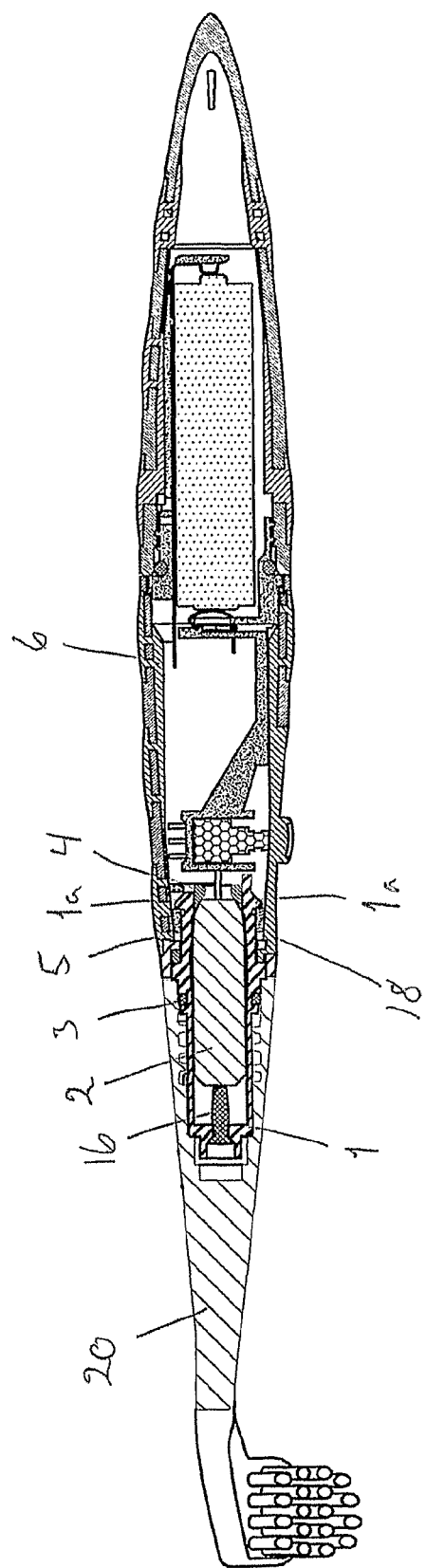
FIG. 3 shows a section of the whole of the electric toothbrush according to the invention.

As can be seen from the figures, an electric toothbrush, according to the invention, comprises a main unit 6 which also functions as the handle of the toothbrush. A flexible covering is arranged around the main unit in the form of, for example, a rubber covering 5. In the main, the rubber covering surrounds most of the main unit 6. At the rear end of the toothbrush an end cover 15 is fastened to the main unit 6, where the end cover also can be covered by a rubber covering 14. The end cover 15 can house a battery 9. To safeguard against ingress of moisture, the end cover is preferably equipped with seals in the form of, for example, one or more O-rings 13. Correspondingly, a frame 8 for the main unit can be equipped with seals in the form of, for example, one or more O-rings 11.

Two electric contacts 10, 12 are connected to an on/off switch 7 in the main unit 6 to control the supply of power to a vibrator motor 2 in a forward part of the main unit 6. The vibrator motor 2 is fitted to a motor frame 1 which is fastened to the main unit 6 with the help of a quick lock 1a in grooves or openings in the forward boring 18 in the main unit 6. To ensure that said quick lock(s) 1a does not come loose from its fastening, a spacer 4 can be arranged internally in the motor frame 1 to secure the quick locks 1a.

According to the invention, an improved vibration is achieved in that the motor 2 is fitted in the motor frame 1 which is not rigidly (or not permanently) fixed to the main unit 6. The motor frame 1 is mounted so that it is at least partially covered by the rubber covering 5 that surrounds the main unit 6. The motor frame 1 can therefore be moved somewhat on the soft rubber which gives an improved vibration effect. Also provided is a dampening so that the vibration, which is transferred to the toothbrush handle, is reduced and gives a seal that prevents ingress of moisture into the unit.

As the motor frame 1 is separated from the main unit 6, this must be fitted to the main unit. This is done with the help of said quick couplings in the form of quick locks 1a that are locked in the grooves or openings. However, the quick lock can lead to that the motor frame is not secured properly and can come loose. The spacer 4 can therefore be fitted internally in the motor frame 1 so that it is nearly impossible for the quick locks to come loose, thereby releasing the motor frame fastened to the main unit. The spacer can be pushed in place after the motor frame is fitted by pressing the motor inwards which in this way presses the spacer in place. A pin 16 is provided to prevent moisture in the form of water entering the area which is formed as the motor is pressed inwards.

A brush head 20 is fitted about the motor frame 1, where seals in the form of one or more O-rings 3 are arranged between the brush head 20 and the main unit 6, and also any other seals and fastenings parts.

The invention claimed is:

1. An electric toothbrush, comprising:
a vibrating brush head coupled to an elongated main unit having a vibrator motor for transfer of vibrating power to the brush head;
a rubber covering surrounding and extending over at least a substantial length of the main unit;
a battery electrically connected to an on/off switch for operation of the vibrator motor, wherein the main unit houses the battery and the on/off switch, the vibrator motor mounted in a motor frame, the motor frame and vibrator motor being non-rigidly secured to the main unit via a quick coupling, and
wherein the motor frame and vibrator motor are at least partially housed by the rubber covering that surrounds the main unit, and the rubber covering covers at least a portion of the motor frame and the vibrator motor to thereby minimize vibration effects to the main unit.

2. The electric toothbrush according to claim 1, wherein the rubber covering is arranged to reduce the vibration that is transferred to the main unit from the vibrator motor.

3. The electric toothbrush according to claim 1, wherein the rubber covering (5), which covers most of the main unit and at least parts of the vibrator motor (2), provides a seal against moisture.

4. The electric toothbrush according to claim 1, wherein the motor frame is fastened to the main unit with one or more quick locks that are forced into grooves or openings in a forward part of the main unit.

5. The electric toothbrush according to claim 4, wherein the motor frame is connected to an internal spacer which is arranged to press against said one or more quick locks for the locking of the motor frame.

6. The electric toothbrush according to claim 1, wherein a pin is arranged inside the motor frame.

* * * * *